(12) United States Patent
Orth (10) Patent No.: US 9,675,431 B2
(45) Date of Patent: Jun. 13, 2017

(54) METHOD FOR DESIGNING A PLURALITY OF ADJACENT TOOTH RESTORATIONS USING CAD/CAM TECHNOLOGY

(75) Inventor: Ulrich Orth, Heppenheim (DE)

(73) Assignee: SIRONA DENTAL SYSTEMS GMBH, Bensheim (DE)

( * ) Notice: Subject to any disclaimer, the term of this patent is extended or adjusted under 35 U.S.C. 154(b) by 1689 days.

(21) Appl. No.: 11/892,221

(22) Filed: Aug. 21, 2007

(65) Prior Publication Data
US 2009/0053677 A1    Feb. 26, 2009

(51) Int. Cl.
*A61C 5/00* (2017.01)
*A61C 13/00* (2006.01)
*A61C 13/225* (2006.01)

(52) U.S. Cl.
CPC ...... *A61C 13/0004* (2013.01); *A61C 13/0006* (2013.01); *A61C 13/225* (2013.01)

(58) Field of Classification Search
CPC ........................................................ A61C 5/00
USPC ..................... 700/97, 117; 433/215, 172, 76
See application file for complete search history.

(56) References Cited

U.S. PATENT DOCUMENTS

| | | | |
|---|---|---|---|
| 5,224,049 A * | 6/1993 | Mushabac | 700/163 |
| 5,343,391 A * | 8/1994 | Mushabac | 433/76 |
| 5,527,182 A * | 6/1996 | Willoughby | 433/172 |
| 6,049,743 A * | 4/2000 | Baba | 700/163 |
| 6,283,753 B1 * | 9/2001 | Willoughby | 433/172 |
| 7,134,874 B2 * | 11/2006 | Chishti et al. | 433/24 |
| 2002/0150859 A1 * | 10/2002 | Imgrund et al. | 433/24 |
| 2004/0253562 A1 * | 12/2004 | Knopp | 433/24 |
| 2005/0144222 A1 * | 6/2005 | Marshall | 709/203 |
| 2005/0177266 A1 * | 8/2005 | Kopelman et al. | 700/117 |
| 2008/0090207 A1 * | 4/2008 | Rubbert | 433/171 |

OTHER PUBLICATIONS

Leinfelder et al., "A new method for generating ceramic restorations: a CAD-CAM system," Journal of the American Dental Assoc., vol. 118, No. 6 (Jun. 1989), pp. 703-707.*

* cited by examiner

Primary Examiner — Tejal Gami
(74) Attorney, Agent, or Firm — Fitzpatrick, Cella, Harper & Scinto (57) ABSTRACT

The invention relates to a method for designing a plurality of adjacent tooth restorations using CAD/CAM technology. In a first step, the virtual model of a first tooth restoration at the first border of the restoration site is designed. In a second step, the virtual model of the second tooth restoration adjacent to the first tooth restoration is designed, the second tooth restoration being adjusted to match the first tooth restoration. The virtual model of the first tooth restoration is adjusted in relation to the second tooth restoration in a third step, if required. This procedure is then repeated for all of the other tooth restorations in the restoration site.

16 Claims, 6 Drawing Sheets

Fig. 12

METHOD FOR DESIGNING A PLURALITY OF ADJACENT TOOTH RESTORATIONS USING CAD/CAM TECHNOLOGY

TECHNICAL FIELD

The invention relates to a method for designing a plurality of adjacent tooth restorations using CAD/CAM technology.

DESCRIPTION OF THE PRIOR ART

A number of methods for designing tooth restorations using CAD/CAM technology has been disclosed in the prior art. Often the tooth restorations are individually designed successively, then carved, possibly veneered, and secured to an appropriately prepared tooth in the patient's oral cavity.

In a refinement thereof, the individual tooth restorations are initially placed in a preparation model of the preparation site in the oral cavity for the purpose of examining them before inserting them directly into the patient's oral cavity. If fitting inaccuracies of the tooth restorations in relation to each other or in relation to the abutment teeth are found, such inaccuracies are corrected.

In the production of bridges, the tooth restorations in the form of bridge members are interconnected using connecting elements and attached to the jaw using bridge anchors, for example, prepared teeth, implants, or inlays. Tooth restorations in the form of crowns have to be produced to fit a basic framework having connecting elements such that they can be placed on the basic framework.

One drawback of this method is that the successive production and insertion of the tooth restorations individually is time consuming and highly complicated.

Another drawback of this method is that, due to planning tolerances and production tolerances, fitting inaccuracies can arise between the tooth restorations. These fitting inaccuracies can be corrected only when the tooth restorations are examined in a preparation model, which is a laborious procedure.

Another drawback is that, in the production of bridges, a basic framework having connecting elements is modeled and produced in a first stage, and the crowns fitting the basic framework are modeled and produced in a second stage. Production tolerances can thus lead to fitting inaccuracies between the basic framework and the crowns.

It is an object of the invention to design a plurality of adjacent tooth restorations using CAD/CAM technology in a time-saving and simple manner involving precise alignment of the individual tooth restorations in relation to each other and, if desired, interconnection thereof to form a bridge.

SUMMARY OF THE INVENTION

This object is achieved by the present invention.

According to the invention, a process is described for designing a plurality of adjacent tooth restorations using CAD/CAM technology, starting from a first border of a restoration site. In a first step, a first tooth restoration is designed at the first border of the restoration site. In a second step, the second tooth restoration is designed, this being adjacent to the first tooth restoration and adjusted to match the first tooth restoration.

The virtual model of the first tooth restoration remains adjustable in relation to the second tooth restoration, and is adjusted in a third step, if necessary.

This procedure is repeated for all of the other tooth restorations on the restoration site until the opposing second border of the restoration site is reached, every additional tooth restoration being adjusted to match the one preceding it, while all of the tooth restorations remain adjustable.

A tooth restoration should imitate the natural tooth as precisely as possible in terms of shape and color impression. The tooth restoration can be a crown for a prepared tooth or for an implant or for an inlay. An inlay is a filling of gold, ceramics, or composite, which is anchored in the tooth and which only partially replaces a natural tooth usually between the crests of the occlusal surface.

The restoration site is that part of the dental arch into which a plurality of adjacent tooth restorations is inserted. This restoration site includes a first border with the first tooth restoration and an opposing second border with the last tooth restoration.

An advantage of this method is that it is possible to first design a plurality of tooth restorations concurrently and fabricate them subsequently. The tooth restorations can thus be adjusted in virtual mode by a user or by computer-aided means to match each other and the abutment teeth.

If the user finds that the position or the size of the tooth restoration can only be achieved if the preceding tooth restoration is changed, then he can select and subsequently adjust the preceding tooth restoration. The fabricated tooth restorations are in the desired alignment in relation to each other and match each other such that no fitting inaccuracies need be corrected.

Advantageously, in the designing phase, a proposed virtual model of a tooth restoration can first be automatically generated using computer-aided design technology, which is adjustable.

This facilitates designing of the tooth restoration since the proposed virtual model requires only slight manual adjustment. The proposed virtual model can already have an occlusal surface designed to mate with the opposing tooth, and a mesial surface and distal surface that are each designed to fit against the abutment tooth or the adjacent tooth restoration. The proposed virtual model can also be selected via computer from a database in which different tooth shapes are stored.

Advantageously, a first abutment tooth can be present outside the restoration site next to the first tooth restoration, which will be adapted to match the first abutment tooth during the designing phase.

The first tooth restoration can thus be adjusted in virtual mode to match the first abutment tooth, thereby eliminating the necessity of being corrected laboriously after fabrication.

A second abutment tooth can advantageously be present next to the last tooth restoration at the second border of, and outside, the restoration site, the last tooth restoration being adapted to match the second abutment tooth during the designing phase.

The last tooth restoration can thus be adjusted in virtual mode to match the second abutment tooth, thereby eliminating the necessity of being corrected laboriously after fabrication.

In another step, it is advantageously possible to select adjacent tooth restorations which are to be interconnected to form a bridge using connecting volumes. Cross-sectional connecting surfaces are then automatically determined and displayed on the selected tooth restorations.

It is thus possible to design a bridge having connecting volumes. A bridge having connecting volumes composed of a plurality of tooth restorations is produced from a single blank of appropriate size, so that connecting volumes are carved between the tooth restorations and the tooth restorations are interconnected. The cross-sectional connecting zones between the tooth restorations constitute the smallest cross-sectional connecting zones of the connecting volumes for a predetermined breaking point. The cross-sectional connecting zones are determined and displayed, for example, using a display device such as a monitor, in order to evaluate them with respect to their size.

The selected tooth restorations with the connecting volumes form a blocking, i.e. they are treated as a single part. This virtual model is thus also referred to as a "blocking".

The connecting volumes can be advantageously designed by shifting the virtual models of adjacent tooth restorations toward each other so that they partially overlap at the contact point and a connecting volume is thus formed.

Tooth restorations are thus interconnected via connecting volumes, without having to change the surface. A slight shift of the virtual model of adjacent tooth restorations toward each other leads to the designs overlapping each other over large areas, particularly in the case of molars. A connecting volume having a cross-sectional connecting zone is thus formed in the gap. This hardly interferes with the aesthetic appearance since the cross-sectional connecting zone in the gap is visible from the outside only to a limited extent.

The connecting volumes can be advantageously designed such that they fill a gap between the virtual models of adjacent tooth restorations and interconnect their lateral surfaces.

The virtual models of adjacent tooth restorations are thus interconnected without having to be shifted. The connecting volume bridges the gap. The connecting volume should be designed as far as possible in that palatal part of the tooth restorations that is directed toward the palate and is not so visible from the outside, in order not to spoil the aesthetic impression.

The size of the automatically proposed cross-sectional connecting zone may advantageously be sufficient to ensure the desired stability of the bridge.

The stability of the bridge having connecting volumes depends on the plastic tensile strength of the material used and the size of the cross-sectional connecting zone at the predetermined breaking point. Thus the size of the cross-sectional connecting zone must be selected such that the bridge can absorb stresses occurring, for example, during chewing without breaking.

Advantageously, the position, alignment, and extent of the cross-sectional connecting zones can be adjustable.

Thus the position, alignment and extent of the cross-sectional connecting zone can be specified with respect to the forces acting when stresses are applied such that the bridge will not break as a consequence of these stresses. The larger the distance of the point of action of said forces from the cross-sectional connecting zone, the greater must be its size on account of the higher torque produced as a vector product of the force and the lever arm of the force.

A blank of appropriate size can be advantageously automatically determined for the bridge, which is carved from this blank using a machining device.

This simplifies the production process by eliminating the requirement of laborious selection of the blank. Instead, the blank is selected automatically based on the dimensions of the planned bridge including the connecting volumes. The advantage of selecting the optimal blank, the boundary surfaces of which are situated as close as possible to the surfaces of the planned bridge, is that the machining time and the volume of material to be removed are reduced.

In another step, adjacent tooth restorations can be advantageously selected which are to be interconnected by connecting elements to form a bridge.

The method of the invention can be used not only on bridges having connecting volumes but also on bridges having connecting elements. The tooth restorations are produced individually and separately from each other and then interconnected using connecting elements. Precisely fitting receiving cavities for the connecting elements are provided in the tooth restorations and are automatically designed. In this way, the tooth restorations are fabricated after the designing phase with high precision in terms of their position, alignment and shape.

The tooth restorations can be advantageously interconnected using connecting elements to form a bridge.

A bridge can thus be fabricated, the interconnected tooth restorations in which are aligned in relation to each other and adapted to match each other. The receiving cavities in the tooth restorations for the connecting elements can be planned automatically by computer-aided means allowing for the position and alignment of the tooth restorations in relation to each other.

At least two tooth restorations can be advantageously attached to bridge anchors and the remaining tooth restorations can serve as intermediate bridge members, it being possible to automatically design receiving cavities on the underside of the tooth restorations using computer-aided design technology, which receiving cavities are made to fit the bridge anchors.

The bridge is thus anchored to the jaw. The bridge anchors should be disposed at equal distances from each other in order to evenly distribute the stresses acting on the bridge. Unsupported bridge members next to a bridge anchor at the end of the bridge should be avoided since this might reduce the stability of the bridge.

The bridge anchors can advantageously be prepared teeth, implants, or inlays.

In the case of a tooth to be prepared, for example, a cove-shaped, tangential or stepped preparation is carved out such that the crown can be secured to this preparation. This crown is connected via a connecting element or connecting volume to the adjacent bridge member. Thus a prepared tooth serves as a bridge anchor. In the case of an implant serving as a bridge anchor, an abutment is usually connected to the implant inserted in the jawbone and a crown is attached to the abutment. This crown can then be connected to the adjacent bridge member. In the case of an inlay serving as a bridge anchor, the inlay anchored in the healthy tooth is connected to the adjacent bridge member by way of a connecting element.

If the first and second abutment teeth are present, the bridge can be advantageously cemented at cementing sites to the first and second abutment teeth using an adhesive method.

The bridge including connecting elements or connecting volumes thus does not require any bridge anchors since the outer tooth restorations of the bridge are cemented to the abutment teeth. The cementing method used can be an expensive etching technique. An advantage of the cemented bridge is that the tooth substance of the abutment teeth is only slightly affected and the aesthetic visual impression of the abutment teeth is retained. Furthermore, there are hardly any stresses acting on the gum.

Advantageously, the bridge is removable.

A removable bridge is based on telescopic crowns which can be detached from the bridge anchors. This facilitates daily hygiene and, if one or more bridge anchors such as prepared teeth or implants are lost, the detachable bridge can be extended and attached to new bridge anchors.

In another step, tooth restorations, which are separate from each other, can be advantageously produced separately.

Individual tooth restorations can thus be produced separately and, after insertion, can be brought into alignment with, and adapted to match, each other in accordance with the virtual model. The tooth restorations can be anchored to the jaw individually and independently of each other.

The tooth restorations are advantageously fabricated concurrently on a plurality of machining devices.

This considerably accelerates the production of the tooth restorations in the form of bridge members having receiving cavities or in the form of separate tooth restorations.

If a single machining device is used, the tooth restorations will be advantageously fabricated successively.

The successive fabrication of tooth restorations can take place automatically using computer-aided design technology. The blanks are automatically clamped in the machining device and machined according to the surface data of the virtual models after such surface data have been transmitted to the machining device. Thus, a plurality of tooth restorations can be fabricated without any manual intervention on the part of the user.

The tooth restorations can be advantageously secured individually to the respective prepared tooth or to an implant.

BRIEF DESCRIPTION OF THE DRAWINGS

Exemplary embodiments of the invention are shown in the drawings, in which.

DESCRIPTION OF PREFERRED
EMBODIMENTS OF THE INVENTION

Figure 1A:
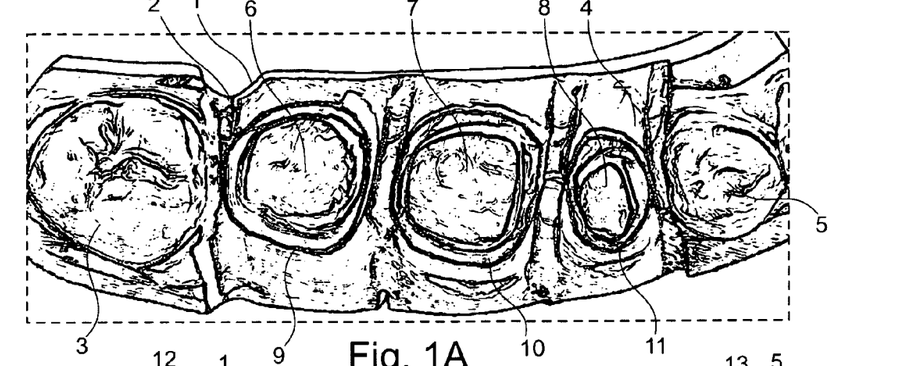
FIG. 1A is a top view of a tooth restoration site.

FIG. 1A is a top view of a restoration site 1 comprising five teeth. A first abutment tooth 3 is located next to the first border 2 of the restoration site 1 and a second abutment tooth 5 is located on the opposing, second border 4 of the restoration site 1. Prepared teeth 6, 7, and 8, which have been prepared for accommodation of tooth restorations, are located between the two abutment teeth 3 and 5. The prepared teeth 6, 7, and 8 have a stepped shape but have not been altered beyond the preparation margins 9, 10, and 11.

Figure 1B:
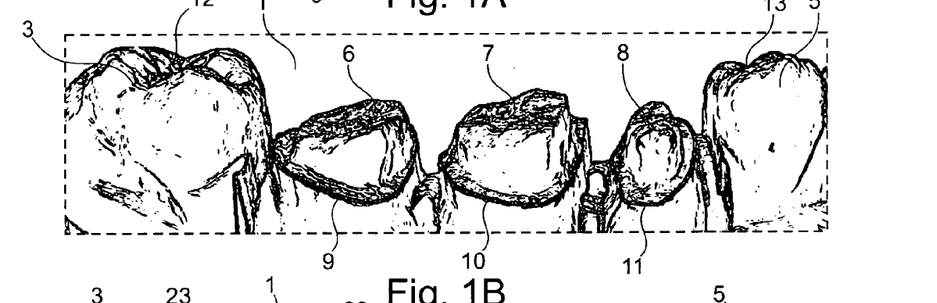
FIG. 1B is a side view of the 3D image shown in FIG. 1A.

FIG. 1B shows a side view of the 3D image shown in FIG. 1A, of the preparation site 1 and the abutment teeth 3 and 5. The restorations for the prepared teeth 6, 7, and 8 must be designed such that they attain the height of the occlusal surface 12 of the abutment tooth 3 and the occlusal surface 13 of the abutment tooth 5 and must fit laterally between the abutment teeth 3 and 5, while their occlusal surfaces must mate with those of the opposing teeth in the opposite jaw (not shown).

Figure 2A:
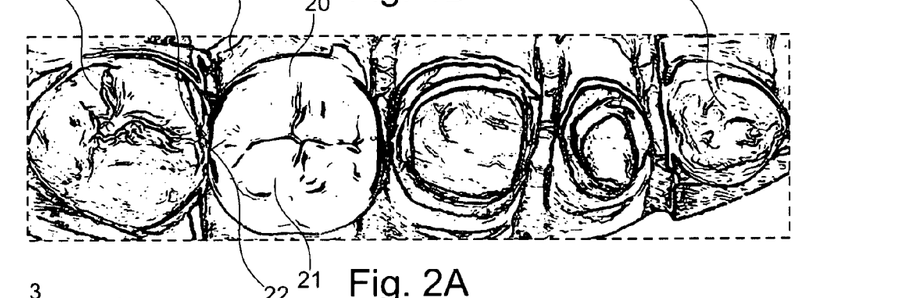
FIG. 2A is a top view of the 3D image shown in FIG. 1A showing a virtual model of a first tooth restoration.

FIG. 2A is a top view of a 3D image of the preparation site 1 and its abutment teeth 3 and 5 shown in FIG. 1A and a virtual model of a first tooth restoration 20 having an occlusal surface 21. During the designing phase, the first tooth restoration 20 was laterally adapted to fit laterally against the first abutment tooth 3. The virtual model of the first tooth restoration was generated automatically by computer-aided means. The occlusal surface 21 is designed to mate with the opposing tooth (not shown). The first tooth restoration is made to match the abutment tooth 3 by tilting and shifting the first tooth restoration 20. A receiving cavity is designed on the underside of the first tooth restoration 20 to mate with the prepared tooth 6 shown in FIG. 1A.

Figure 2B:
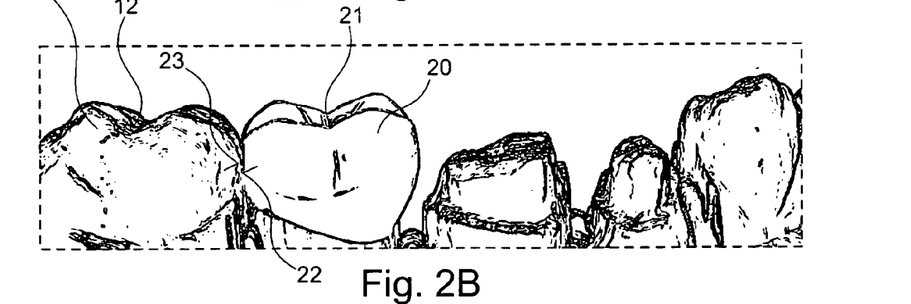
FIG. 2B is a side view of the 3D image shown in FIG. 2A.

FIG. 2B is a side view of the 3D image shown in FIG. 2A, showing the first tooth restoration 20. The occlusal surface 21 is at the same level as the occlusal surface 12 of the abutment tooth 3. The first tooth restoration 20 has been adapted to fit the first abutment tooth 3 such that there is no gap between that lateral distal surface 22 of the first tooth restoration 20 that is directed toward the end of the dental arch and that lateral mesial surface 23 of the abutment tooth 3 that is directed towards the center of the dental arch.

Figure 3A:
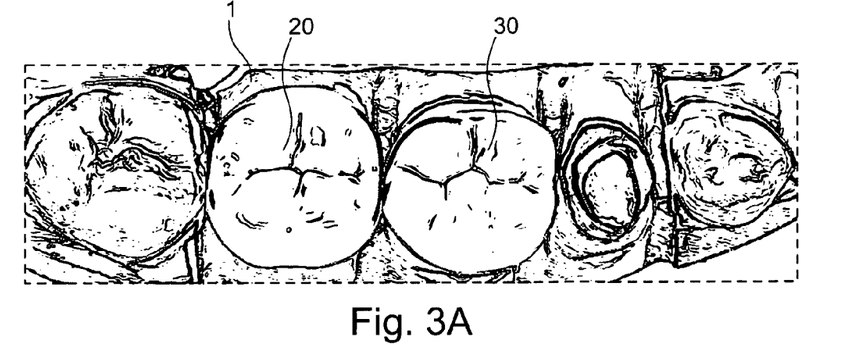
FIG. 3A is a top view of the 3D image shown in FIG. 2A showing a virtual model of a second tooth restoration.

FIG. 3A is a 3D image of the preparation site 1 shown in FIG. 2A, showing the virtual model of the first tooth restoration 20 and the virtual model of the second tooth restoration 30. The second tooth restoration 30 has been adapted to laterally fit against the first tooth restoration. The second tooth restoration 30 is designed automatically by computer-aided means. The second tooth restoration is tilted and shifted slightly so as to make it fit laterally against the first tooth restoration, the receiving cavity on the underside of the second tooth restoration being modified to make it correspond to the prepared tooth 7.

Figure 3B:
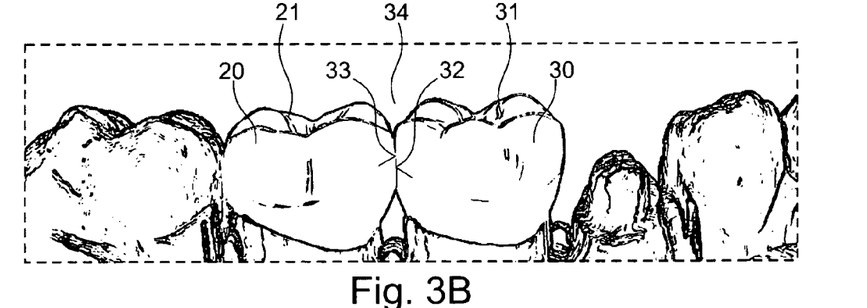
FIG. 3B is a side view of the 3D image shown in FIG. 3A.

FIG. 3B is a side view of the 3D image shown in FIG. 3A. The occlusal surface 31 of the second tooth restoration is at the same level as the occlusal surface 21 of the first tooth restoration 20. The lateral distal surface 32 of the second tooth restoration 30 has contact points with the mesial surface 33 of the first tooth restoration 20. While it is being adapted laterally, the second tooth restoration 30 can be made to overlap the first tooth restoration 20 slightly so that a cross-sectional connecting area 34 on the contact side between the second tooth restoration 30 and the first tooth restoration 20 is enlarged. In this way it is possible to ensure the desired stability of the bridge when fabricating a bridge having connecting volumes. In a bridge having connecting volumes, the tooth restorations are carved jointly from a blank of appropriate size using a machining device, connecting volumes being carved between the tooth restorations, said connecting volumes having cross-sectional connecting areas of the size required to achieve the desired stability of the bridge. Unlike conventional bridges, the bridge members are held together by connecting volumes instead of a framework made of connecting elements. The virtual model of the first tooth restoration 20 remains adjustable and can be selected and adjusted in relation to the first abutment tooth and to the virtual model of the second tooth restoration 30, if necessary.

Figure 4A:
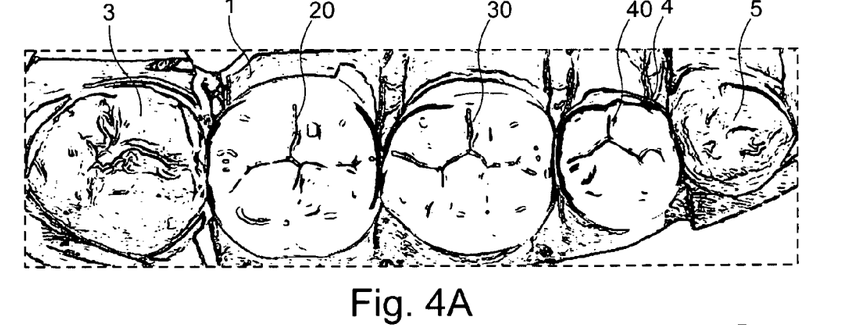
FIG. 4A is a top view of the 3D image shown in FIG. 3A showing a virtual model of a third tooth restoration.

FIG. 4A is a top view of a 3D image as shown in FIG. 3A, showing a third tooth restoration 40. The third tooth restoration 40 is adjusted, like the second tooth restoration in the manner described in connection with FIGS. 3A and 3B, to make it fit laterally against the preceding tooth restoration, namely the second tooth restoration 30. The third tooth restoration 40 is the last one in the row and is located, when viewed in the mesial direction from the first border 2, at the second opposing border 4 of the preparation site 1 and is adjacent to the second abutment tooth 5.

Figure 4B:
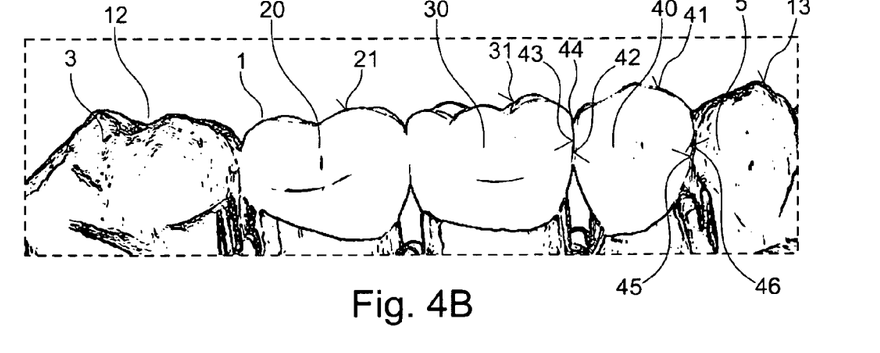
FIG. 4B is a side view of the 3D image shown in FIG. 4A.

FIG. 4B is a side view of the 3D image of the preparation site 1 and the virtual models of tooth restorations 20, 30, and 40 shown in FIG. 4A. The occlusal surface 41 of the third tooth restoration 40 is at the same level as the other occlusal surfaces 12, 21, 31, and 13. The third tooth restoration 40 was also designed automatically in the form of a restoration model by computer-aided means on the basis of the surface data of the opposing teeth, the abutment tooth 5, and the second tooth restoration 30.

The third tooth restoration 40 is tilted and shifted laterally to make it fit against the abutment tooth 5 and the second tooth restoration 30. Between the distal surface 42 of the third tooth restoration 40 and the mesial surface 43 of the second tooth restoration 30 a cross-sectional connecting zone 44 is located at contact sites, the dimensions of the cross-sectional connecting zone being made large enough to achieve the desired stability of the bridge. The third tooth restoration 40 is adapted such that its mesial surface 45 abuts closely against the distal surface 46 of the second abutment tooth 5. The first and second tooth restorations 20 and 30 remain variable and adjustable, as necessary.

Figure 5:
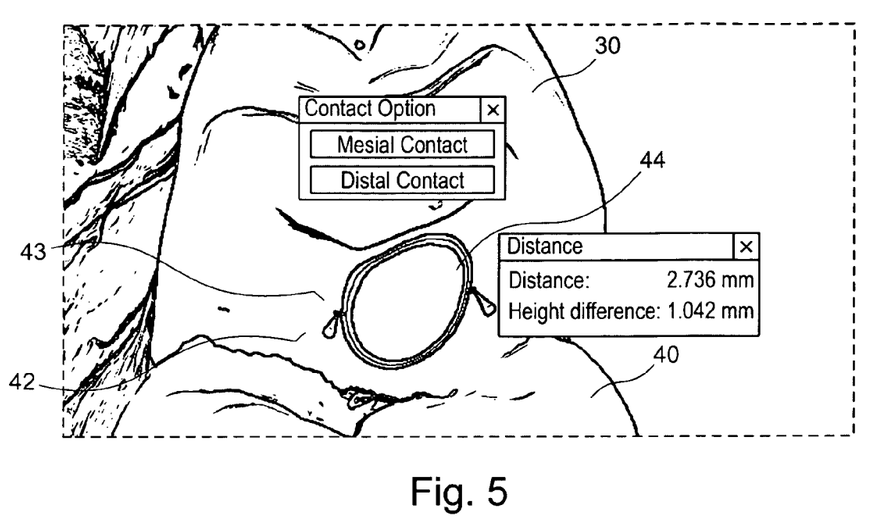
FIG. 5 shows the cross-sectional connecting zone viewed obliquely from above.

FIG. 5 shows the cross-sectional connecting zone 44, viewed obliquely from above, between the second tooth restoration 30 and the third tooth restoration 40. The distal half of the third tooth restoration 40 is not shown in order to permit an unobstructed view of the cross-sectional connecting zone 44. The cross-sectional connecting zone 44 has an almost circular shape and would form the predetermined breaking point of the bridge between the tooth restorations 30 and 40, should the bridge be subjected to excessive load. The cross-sectional connecting zone 44 must be large enough for it to ensure the desired stability of the bridge and absorb the stresses arising during chewing without breaking. The necessary dimensions of the cross-sectional connecting zone 44 are mainly determined by the properties of the material used, the forces arising under load and the distance of the points of application of these forces from the cross-sectional connecting zone 44. In the case of a large distance between the points of application of the resulting forces and the cross-sectional connecting zone 44, the torque arising as the vector product of the force and the lever arm of the force would be higher so that the size of the cross-sectional connecting zone 44 would have to be increased. Alternatively, the position, alignment, and extent of the cross-sectional connecting zone 44 may be adjusted. When the second and third tooth restorations 30 and 40 are moved toward each other, the cross-sectional connecting zone 44 increases, thereby enhancing the stability of the bridge. Furthermore, it is possible to connect the second tooth restoration at the point of contact thereof with the third tooth restoration by means of a connecting volume that is carved during the machining operation. The shape of this connecting volume does not correspond to an interdental space as in the case of natural teeth. Rather, it corresponds to an arcuate transition between the distal surface 43 and the mesial surface 42. It is thus possible to modulate and expand the cross-sectional connecting zone 44. When designing the bridge, allowance is made for the fact that it will have connecting volumes between the tooth restorations 20, 30, and 40 and will be carved from a single blank of appropriate size by means of a machining device. The machining device uses a grinding tool having a defined diameter, for example, a diameter of 0.8 mm. Accordingly, during this type of machining, connecting volumes having a width of at least the width of the grinding tool are inevitably carved, thereby ensuring the desired stability of the bridge. However, other production processes are possible.

Figure 6:
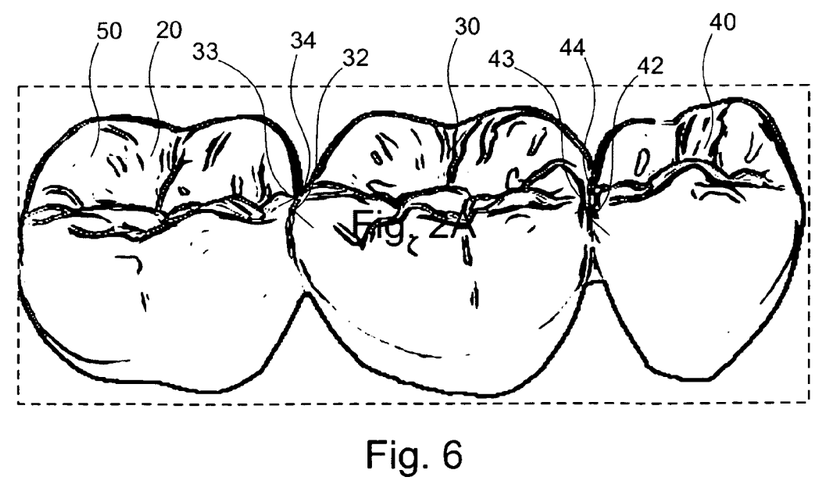
FIG. 6 shows a fabricated bridge having connecting volumes corresponding to the virtual model shown in FIG. 4A.

FIG. 6 shows the fabricated bridge 50 with connecting volumes corresponding to the virtual models of the tooth restorations 20, 30, and 40. The bridge 50 was milled from a single blank of suitable size by means of a machining device. A connecting volume including the cross-sectional connecting zone 34 is shown between the distal surface 33 and the mesial surface 32, and a second connecting volume including the cross-sectional connecting zone 44 is shown between the distal surface 43 and the mesial surface 42. On their undersides, the tooth restorations 20, 30, and 40 have receiving cavities such that they can be fitted to the prepared teeth 6, 7, and 8.

Figure 7:
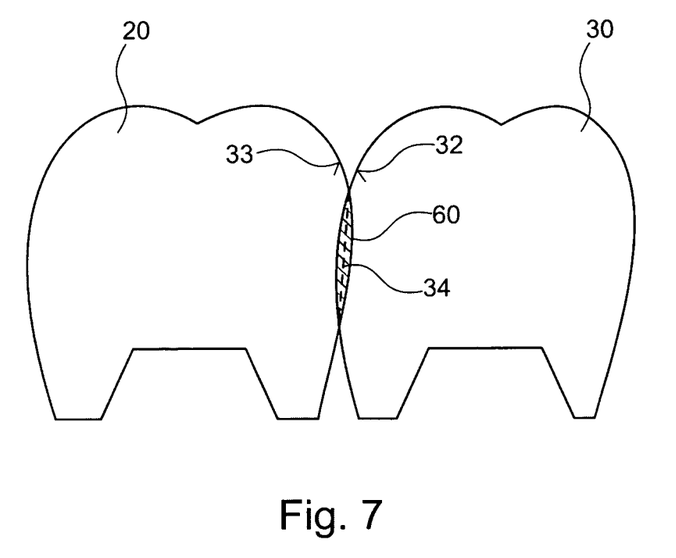
FIG. 7 shows the virtual model of a connecting volume achieved by displacing the adjacent virtual models of tooth restorations.

FIG. 7 shows two adjacent virtual models of tooth restorations 20 and 30. During the designing process, the second tooth restoration 30 is shifted toward the first tooth restoration 20 so that the virtual models of the tooth restorations 20 and 30 partially overlap and a connecting volume 60 having a cross-sectional connecting zone 34 is formed at the point of contact between the mesial surface 33 and the distal surface 32.

Figure 8:
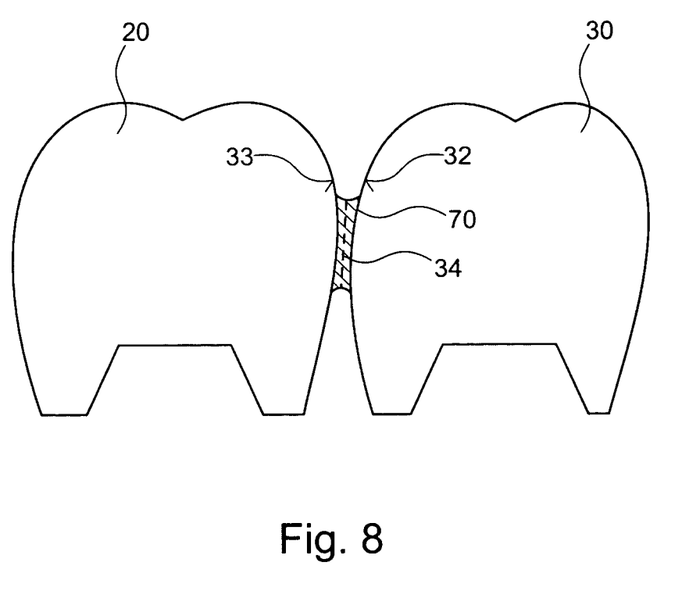
FIG. 8 shows the virtual model of a connecting volume in the form of a dental gap-filler situated between the adjacent virtual models of tooth restorations.

FIG. 8 shows two adjacent virtual models of tooth restorations 20 and 30 as shown in FIG. 7. A connecting volume 70 having a cross-sectional connecting zone 34 is designed so as to bridge the gap between the mesial surface 33 and the distal surface 32 and to interconnect the two virtual models of tooth restorations 20 and 30. Unlike the method illustrated in FIG. 7, the virtual models of the tooth restorations 20 and 30 are not shifted.

Figure 9:
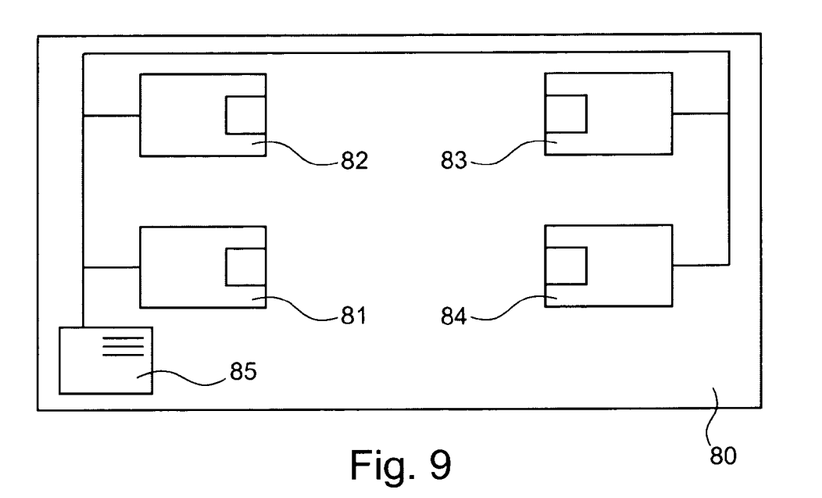
FIG. 9 shows a production chamber comprising four machining devices.

FIG. 9 shows a production chamber 80, in which four machining devices 81, 82, 83, and 84 and a server 85 are located. After tooth restorations 20, 30, and 40 of FIG. 4A have been designed by means of a computer, the design data are transmitted to the server 85, which distributes the design data of the individual tooth restorations 20, 30, and 40 to the four machining devices 81, 82, 83, and 84. In the next step, each of the machining devices 81, 82, 83, and 84 then simultaneously produces the tooth restoration assigned thereto. The duration of the production process is thus four times shorter than the successive production of tooth restorations using only one machining tool.

Figure 10:
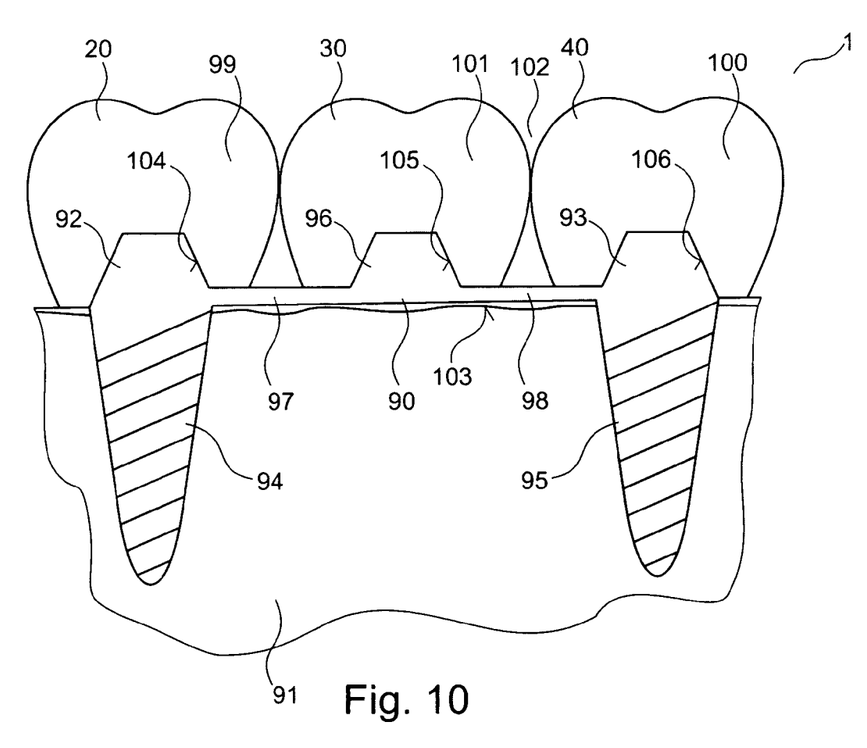
FIG. 10 shows tooth restorations, as shown in FIG. 4B, which are anchored to the jaw by means of a bridge framework.

FIG. 10 shows tooth restorations 20, 30, and 40 as shown in FIG. 4B, which are anchored to the jaw 91 via a bridge frame 90 instead of via prepared teeth. The tooth restorations 20 and 30 are connected to frame members 92 and 93, which are attached to implants 94 and 95.

These implants 94 and 95 are bridge anchors and are permanently fitted to the jaw 91. The tooth restoration 30 is attached to the frame member 96, which is not anchored to the jaw but is instead connected on both sides to the frame members 92 and 93 by means of connecting elements 97 and 98. The tooth restorations 20, 30, 40 and the frame members 92, 93, 96 form the outer anchored bridge members 99 and 100 and an intermediate bridge member 101 that is not anchored. The bridge members 99, 100, and 101 are parts of a bridge 102 having connecting elements 97 and 98. The tooth restorations 99, 100, and 101 comprise receiving cavities 104, 105, and 106 on their side facing the gum surface 103. These receiving cavities 104, 105, and 106 are automatically designed by computer-aided means and match the frame members 92, 93, and 96 and the connecting elements 97 and 98. A 3D image of the preparation site already fitted with the bridge framework 90 is used for designing the tooth restorations 20, 30, 40. The receiving cavities 104, 105, and 106 are automatically designed in the form of counter-surfaces mating with the surfaces of the frame members 92, 93, 96 and the connecting elements 97 and 98. The tooth restorations 20, 30, and 40 are simultaneously automatically produced by means of the machining devices 81, 82, and 83 or successively by means of one machining device 81, shown in FIG. 9.

Figure 11:
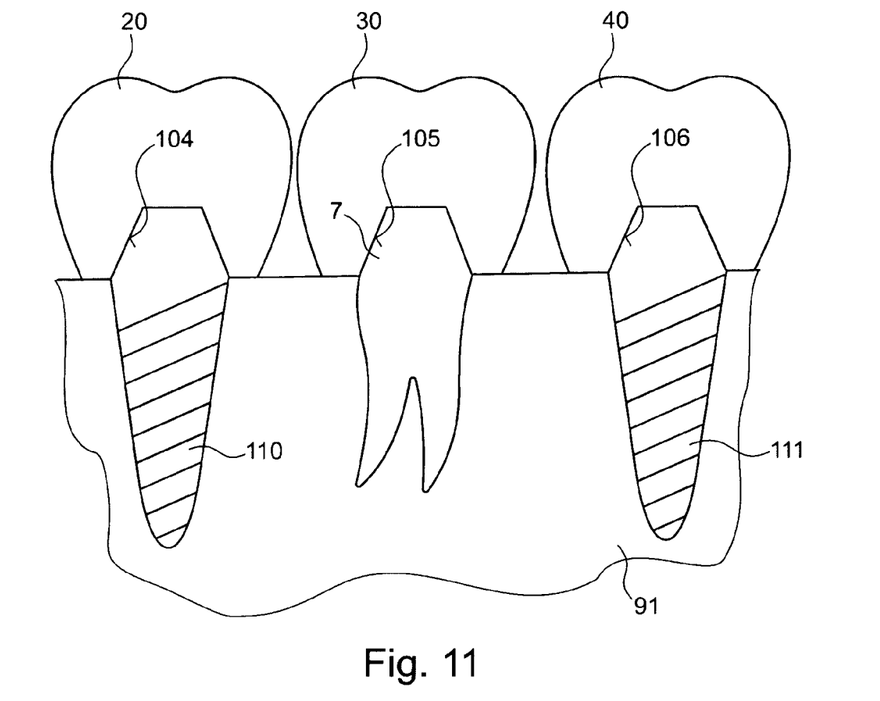
FIG. 11 shows tooth restorations, as shown in FIG. 4B, which are individually anchored to the jaw.

FIG. 11 shows the tooth restorations 20, 30, and 40 as shown in FIG. 4B. Unlike FIG. 10 or FIG. 6, the tooth restorations 20, 30, and 40 are not interconnected in FIG. 11. Instead, they are anchored individually to the jaw 91. The outer tooth restorations 20 and 40 are anchored to the jaw 91 by means of implants 110, 111, and the middle tooth restoration 30 is anchored to the jaw 91 by means of the prepared tooth 7. The receiving cavities 104, 105, 106 are automatically designed in the form of counter-surfaces to the surfaces of the implants 110, 111 and the prepared tooth 7. The tooth restorations 20, 30, and 40 having the receiving cavities 104, 105, 106 are automatically produced separately from each other and simultaneously by means of the machining devices 81, 82, and 83 respectively or successively by means of one machining device 81, shown in FIG. 9.

Figure 12:
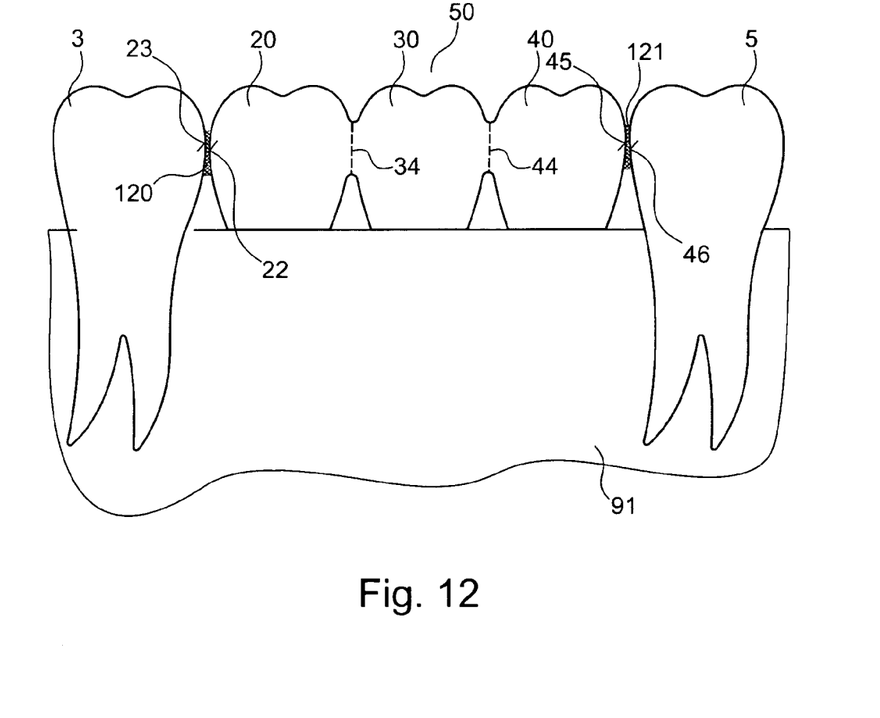
FIG. 12 shows tooth restorations, as shown in FIG. 4B, which are cemented to the abutment teeth by a cementing method.

FIG. 12 shows the tooth restorations 20, 30, and 40 as shown in FIG. 4B. In FIG. 12, the tooth restorations 20, 30 and 40 are interconnected by means of connecting volumes having cross-sectional connecting zones 34 and 44 to form a bridge 50, which is produced from a single blank of appropriate size by means of the machining device 81 shown in FIG. 9. Unlike FIG. 4B, FIG. 10, and FIG. 11, the tooth restorations 20, 30, and 40 are not anchored to the jaw 91. Instead, the tooth restorations 20, 30, and 40 are cemented to the abutment teeth 3 and 5 by a cementing method. This technique protects the tooth substance of healthy teeth and the gum from damage. The first cementing site 120 is located between the mesial surface 23 of the first abutment tooth 3 and the distal surface 22 of the first tooth restoration 20. The second cementing site 121 is located between the mesial surface 45 of the third tooth restoration 40 and the distal surface 46 of the second abutment tooth 5.

LIST OF REFERENCE NUMERALS 1 restoration site
2 first border
3 first abutment tooth
4 second border
5 second abutment tooth
6 first prepared tooth
7 second prepared tooth
8 third prepared tooth
9 first preparation margin
10 second preparation margin
11 third preparation margin
12 first occlusal surface
13 second occlusal surface
20 first tooth restoration
21 occlusal surface
22 distal surface
23 mesial surface
30 second tooth restoration
31 occlusal surface
32 distal surface
33 mesial surface
34 cross-sectional connecting zone
40 third tooth restoration
41 occlusal surface
42 distal surface
43 mesial surface
44 cross-sectional connecting zone
45 mesial surface
46 distal surface
50 bridge
60 connecting volume
70 connecting volume
80 production chamber
81, 82, 83, and 84 machining devices
85 server
90 bridge framework
92 and 93 frame members
94 and 95 implants
96 frame member
97 and 98 connecting elements
99 and 100 bridge members
101 intermediate bridge member
102 bridge
103 gum surface
104, 105 and 106 receiving cavities
110, 111 implants
120 first cementing site
121 second cementing site

The invention claimed is:

1. A method for designing tooth restorations, comprising:
generating a plurality of virtual models respectively corresponding to a plurality of artificial tooth restorations for a dental restoration site, wherein each of the plurality of virtual models is adjustable relative to at least another virtual model of the plurality of virtual models; and
adjusting a second virtual model of the plurality of virtual models relative to a first virtual model of the plurality of virtual models by tilting and/or shifting the second virtual model with respect to the first virtual model such that the first virtual model and the second virtual model at least partially overlap to form a connecting volume.

2. The method according to claim 1, further comprising:
adjusting a third virtual model of the plurality of virtual models relative to a virtual model of an abutting tooth located outside of the dental restoration site and adjacent to a last tooth restoration corresponding to the third virtual model by tilting and/or shifting the third virtual model relative to the virtual model of the abutting tooth.

3. The method according to claim 1, further comprising:
determining a size of the connecting volume by automatically determining a cross-sectional connecting zone between the first virtual model and the second virtual model.

4. The method according to claim 1, wherein the connecting volume is formed at a point of contact between a mesial surface of the first virtual model and a distal surface of the second virtual model.

5. The method as defined in claim 3, further comprising:
determining dimensions of the cross-sectional connecting zone based on: (i) a material from which the plurality of artificial tooth restorations are formed, (ii) a calculation of the forces applied to the material under load, and (iii) distances from respective points of application of the forces to the cross-sectional connecting zone.

6. The method according to claim 3, wherein at least one of a position, an alignment, and a size of the cross-sectional connecting zone is adjustable.

7. The method according to claim 5, further comprising:
automatically selecting a blank of the material from which the plurality of artificial tooth restorations are to be formed; and
carving the plurality of artificial tooth restorations from the blank based on the plurality of virtual models using a machining device.

8. A method for designing tooth restorations, comprising:
generating a plurality of virtual models respectively corresponding to a plurality of artificial tooth restorations for a dental restoration site, wherein each of the plurality of virtual models is adjustable relative to at least another virtual model of the plurality of virtual models;
selecting at least two virtual models corresponding to two adjacent tooth restorations to be interconnected via a connecting element to form a bridge; and
modifying the at least two virtual models corresponding to the two adjacent tooth restorations to be interconnected such that the at least two virtual models include respective receiving cavities, each receiving cavity configured to receive the connecting element.

9. The method according to claim 8, further comprising:
interconnecting the at least two virtual models of the at least two adjacent tooth restorations via a virtual connecting element to form a virtual bridge.

10. The method according to claim 9, further comprising:
carving a bridge using a carving machine based the virtual bridge formed from the at least two virtual models that have been modified to include the respective receiving cavities.

11. The method according to claim 1, wherein the first virtual model corresponds to a first tooth restoration disposed at a distal end of the dental restoration site adjacent to an abutting tooth, and
wherein the first virtual model is adjusted relative to a virtual model of the abutting tooth such that there is no distance between a lateral distal surface of the first virtual model and a lateral mesial surface of the virtual model of the abutting tooth.

12. The method according to claim 11, wherein the first virtual model is laterally adapted to fit against the virtual model of the abutting tooth so that there is no distance between the lateral distal surface of the first virtual model and the lateral mesial surface of the virtual model of the abutting tooth.

13. The method according to claim 1, wherein the plurality of virtual models are generated such that the plurality of artificial tooth restorations have occlusal surfaces designed to mate with opposing teeth.

14. The method according to claim 1, wherein each of the plurality of virtual models is generated to include a corresponding receiving cavity disposed on an underside of the virtual model and configured to mate with a corresponding prepared tooth.

15. An apparatus for designing tooth restorations, comprising:
a processor; and
a memory storing at least one control program, wherein the processor and memory are operably configured to:
generate a plurality of virtual models respectively corresponding to a plurality of artificial tooth restorations for a dental restoration site, wherein each of the plurality of virtual models is adjustable relative to at least another virtual model of the plurality of virtual models; and
adjust a second virtual model of the plurality of virtual models relative to a first virtual model of the plurality of virtual models by tilting and/or shifting the second virtual model with respect to the first virtual model such that the first virtual model and the second virtual model at least partially overlap to form a connecting volume.

16. An apparatus for designing tooth restorations, comprising:
a processor; and
a memory storing at least one control program, wherein the processor and memory are operably configured to:
generate a plurality of virtual models respectively corresponding to a plurality of artificial tooth restorations for a dental restoration site, wherein each of the plurality of virtual models is adjustable relative to at least another virtual model of the plurality of virtual models;
select at least two virtual models corresponding to two adjacent tooth restorations to be interconnected via a connecting element to form a bridge; and
modify the at least two virtual models corresponding to the two adjacent tooth restorations to be interconnected such that the at least two virtual models include respective receiving cavities, each receiving cavity configured to receive the connecting element.

* * * * *